US012280238B2

(12) United States Patent
Skoller et al.

(10) Patent No.: US 12,280,238 B2
(45) Date of Patent: Apr. 22, 2025

(54) IV ADMINISTRATION SYSTEM CONFIGURED TO PREVENT SELF-INFLICTED INJURY

(71) Applicant: Emory University, Atlanta, GA (US)

(72) Inventors: Nathan J. Skoller, Atlanta, GA (US); Rush Austin Leigh, Atlanta, GA (US); Tamera Tyra Mason, Atlanta, GA (US); Rachael Elizabeth Price, Atlanta, GA (US); Ian Smith, Atlanta, GA (US)

(73) Assignee: Emory University, Atlanta, GA (US)

( * ) Notice: Subject to any disclaimer, the term of this patent is extended or adjusted under 35 U.S.C. 154(b) by 1189 days.

(21) Appl. No.: 16/953,697

(22) Filed: Nov. 20, 2020

(65) Prior Publication Data
US 2021/0154400 A1    May 27, 2021

Related U.S. Application Data

(60) Provisional application No. 62/940,361, filed on Nov. 26, 2019.

(51) Int. Cl.
*A61M 5/162* (2006.01)
*A61M 5/14* (2006.01)
*A61M 5/145* (2006.01)

(52) U.S. Cl.
CPC .......... *A61M 5/162* (2013.01); *A61M 5/1411* (2013.01); *A61M 5/145* (2013.01); *A61M 2005/14506* (2013.01)

(58) Field of Classification Search
CPC .... A61M 5/1411; A61M 5/162; A61M 5/145; A61M 5/02; A61M 2005/14506;
(Continued)

(56) References Cited

U.S. PATENT DOCUMENTS 2,969,063 A    1/1961    Broman
5,738,923 A    4/1998    Ko et al.
(Continued)

FOREIGN PATENT DOCUMENTS

EP        0 873 759 B1     6/2005
WO    WO 2001045771 A1    6/2001

OTHER PUBLICATIONS

Garros et al. "Strangulation With Intravenous Tubing: A Previously Undescribed Adverse Advent in Children." Pediatrics. 2003; 111(6): e732-e734.

*Primary Examiner* — Bradley J Osinski
(74) *Attorney, Agent, or Firm* — Emory Patent Group (57) ABSTRACT

The devices and systems can allow for safe and cost-effective administration intravenous medication, for example, in psychiatric settings by mitigating ligature, disassembly, and weaponization risks associated with intravenous administration. The system may include a fluid connection device. The fluid connection device may include an internal conduit configured to deliver a medical fluid and a housing disposed in which the internal conduit is disposed. The housing may include a first rigid segment and a second rigid segment spaced from the first rigid segment. The housing may also include a first joint segment disposed between the first rigid segment and the second rigid segment and configured to bend to the predetermined bending angle with respect to the first rigid segment.

19 Claims, 11 Drawing Sheets

(58) Field of Classification Search
CPC .... A61M 2025/024; A61M 2025/0246; A61M 2039/1066; A61M 39/1011; A61M 39/1055
See application file for complete search history.

(56) References Cited

U.S. PATENT DOCUMENTS

| | | | |
|---|---|---|---|
| 6,261,267 B1 * | 7/2001 | Chen ................. | A61M 5/40 |
| | | | 604/254 |
| 6,726,672 B1 | 4/2004 | Hanly et al. | |
| 6,958,055 B2 | 10/2005 | Donnan et al. | |
| 7,361,169 B2 | 4/2008 | Reilly | |
| 7,913,692 B2 | 3/2011 | Kwok | |
| 8,167,844 B2 | 5/2012 | Dillard, III | |
| 8,460,272 B2 | 6/2013 | Kudo | |
| 9,227,046 B1 | 1/2016 | Douglas | |
| 9,358,333 B2 | 6/2016 | Trombley, III et al. | |
| 10,149,937 B2 | 12/2018 | Hanner et al. | |
| 2004/0204699 A1 | 10/2004 | Hanly et al. | |
| 2006/0249635 A1 | 11/2006 | Newkirk et al. | |
| 2007/0043326 A1 * | 2/2007 | Navarro ............ | A61M 25/02 |
| | | | 604/264 |
| 2011/0004153 A1 * | 1/2011 | Kipping ............ | A61M 25/00 |
| | | | 604/65 |
| 2016/0367789 A1 * | 12/2016 | Beran ............... | A61M 25/02 |

* cited by examiner

IV ADMINISTRATION SYSTEM CONFIGURED TO PREVENT SELF-INFLICTED INJURY

CROSS-REFERENCE TO RELATED APPLICATIONS

This application claims the benefit of U.S. Provisional Application No. 62/940,361 filed Nov. 26, 2019. The entirety of this reference is hereby incorporated by reference for all purposes.

BACKGROUND

Currently available intravenous (IV) administrative systems, e.g., intravenous tubes and/or spikes, generally provide significant safety risks to patients who have psychiatric and/or medical illness, as well as clinical staff. For example, the risks may include but are not limited to ligature risk, tamper (e.g., disassembly) risk, weaponization risk, etc. These patients can require significant healthcare resources (e.g., extra staffing, prolonged lengths of stay, interfacility transfers, etc.) to safely manage these risks. For example, during the administration of IV medications, extra staff is often required to closely monitor patients through one-to-one observation to prevent self-harm. Employing extra staff for these circumstances can be costly and often impractical. These risks can thus compromise the care of a patient as well as burden the medical facility.

SUMMARY

Thus, there is a need for systems and devices that can safely and cost effectively administer intravenous medication without compromising the care of a patient, for example, in psychiatric settings.

This disclosure is directed to systems and devices that can allow for safe administration intravenous medication. By mitigating the ligature, disassembly, and weaponization risks associated with intravenous administration, intravenous medication administrated using the disclosed systems and devices can safely be performed on patients, who have psychiatric and/or medical illness, without requiring additional resources. Thus, reducing the financial and staff burdens associated with caring for these patients.

In some embodiments, the systems may include an intravenous administration system. In some embodiments, the intravenous administration system may include a fluid connection device having a first end, a second end, and a length. In some embodiments, the fluid connection device may include an internal conduit configured to deliver a medical fluid and disposed along the length. The fluid connection device may also include a housing disposed along the length and have a channel in which the internal conduit is disposed. In some embodiments, the housing may include more than one rigid segments. Each rigid segment may be an elongated segment. In some embodiments, the more than one rigid segments may include a first rigid segment and a second rigid segment spaced from the first rigid segment. In some embodiments, the housing may include one or more joint segments. Each joint segment may be an elongated segment configured to bend to a predetermined bending angle with respect to at least one rigid segment. In some embodiments, the one or more joint segments may include a first joint segment disposed between the first rigid segment and the second rigid segment and configured to bend to the predetermined bending angle with respect to the first rigid segment.

In some embodiments, the intravenous administration system may include an access device. The access device may be configured to connect to one end of a fluid connection device. In some embodiments, the access device may include a spike member. The spike member may include a puncturing tip. In some embodiments, the access device may further include a base member. The base member may include a body and a shaft extending from the body. In some embodiments, the spike member may be disposed within the shaft in a first state and may be configured to permanently move from the first state to a second state with respect to the shaft.

In some embodiments, the administration system may include the fluid connection device and the access device.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

FIGS. 2A-C show views of a fluid connection device shown in FIG. 1 according to embodiments. FIG. 2A shows the fluid connection device shown in FIG. 1 according to embodiments; FIG. 2B shows a top view of the fluid connection device shown in FIG. 2A.

FIGS. 3A-C show views of an access device shown in FIG. 1 having a spike member configured to breakaway in a default state according to embodiments; FIG. 3A shows the access device in the default state according to embodiments; FIG. 3B shows a top view of the access device shown in FIG. 3A.

FIG. 4A shows the access device shown in FIGS. 3A-C in the breakaway state according to embodiments.

FIGS. 5A-C show views of an access device shown in FIG. 1 having a spike member configured to retract in a default state according to embodiments; FIG. 5A shows the access device in the default state according to embodiments; FIG. 5B shows a top view of the access device shown in FIG. 5A.

FIG. 6A shows the access device shown in FIGS.

5A-C in the retractable state according to embodiments.

DESCRIPTION OF THE EMBODIMENTS

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The systems and devices of the disclosure relate to systems and devices that may be configured to be used for intravenous or medical fluid treatments. The systems and devices of the disclosure have features that can mitigate the significant risks, such as ligature (e.g., a ligature that can be used to bind or tie something tightly, causing strangulation or disrupting circulation), weaponization and disassembly (e.g., by patients for harm to self or others) risks, associated with unmonitored use of intravenous administration systems, for example, in a psychiatric setting.

In some embodiments, the systems and devices of the disclosures may include a fluid connection device that includes a housing and a fluid conduit (e.g., a tube) configured to deliver a medical fluid from, for example, a medical fluid container or bag. In some embodiments, the fluid connection device may include a fluid conduit (or "tube" or "tubing") and a housing surrounding the fluid conduit. In some embodiments, the systems and devices of the disclosures may also include a fluid access device (e.g., a spiking device) (also referred to as "access device") (i) connected to or configured to connect to a fluid connection device and (ii) configured to puncture a medical fluid container or bag (e.g., an IV bag or container). In some embodiments, the system and/or the fluid connection device and/or the fluid access device may include features that address the ligature, weaponization, and/or disassembly risks.

For example, with regards to the fluid connection device, the housing may be configured to limit the flexibility of the tubing. In some embodiments, the housing may include more than one rigid segment and a joint segment disposed between two rigid segments. The joint segment may be an elongated segment configured to bend to a predefined or predetermined bending angle with respect to one of the rigid segments. In some embodiments, the predetermined bending angle may be about 30 degrees to about 70 degrees. In some embodiments, the predetermined bending angle may be no more than 70 degrees. By limiting the flexibility of the housing to the predetermined bending angle, strangulation by ligature should not be mechanically possible.

For example, the housing of the fluid connection device may also have features that address potential weaponization risks. In some embodiments, each of the rigid segments may have dimensions that may be configured to slow the speed of articulation at the joint segment so as to reduce potential whip-like actions.

By way of another example, the fluid access device may include features that inhibit access to a sharp point to mitigate the risk of the weaponization. In some embodiments, the fluid access device may include a spike member having a puncture point configured to puncture a medical fluid container via its port. The spike member may be configured (i) to breakaway so as to remain in the port of the fluid container and/or (ii) to retract within the access device so at prevent access to the puncturing point of the spike member if the system is pulled from the medical fluid container by the patient.

By way of another example, the devices and/or systems of the disclosure may be manufactured so as to not to have certain devices/members capable of being disassembled so as to prevent the risk of self-harm by the patient using the disassembled components. This way, those devices (e.g., fluid connection device)/members of those devices cannot be easily damaged, interfered with, or taken apart.

By mitigating these risks, the systems and/or devices of the disclosure can reduce the need for maintaining adequate staffing, interfacility transfers, and prolonged lengths of stay. Thus, the systems and devices of the disclosure can reduce significant financial and resource burdens related to treating patients who may have medical and/or psychiatric illness.

FIGS. 1-7 show examples of a system, a fluid connection device, and fluid access devices, according to some embodiments. It will be understood that the fluid connection systems are not limited to the configuration and/or combination of the fluid connection device and fluid access devices as shown and described with respect to the figures. The systems may include any combination of the features of the devices as shown and described, as well as additional and/or alternative features. For example, the fluid connection device and the fluid access devices, as shown and described, may also be configured to be used with other fluid access devices and fluid connection devices, respectively.

Figure 1:
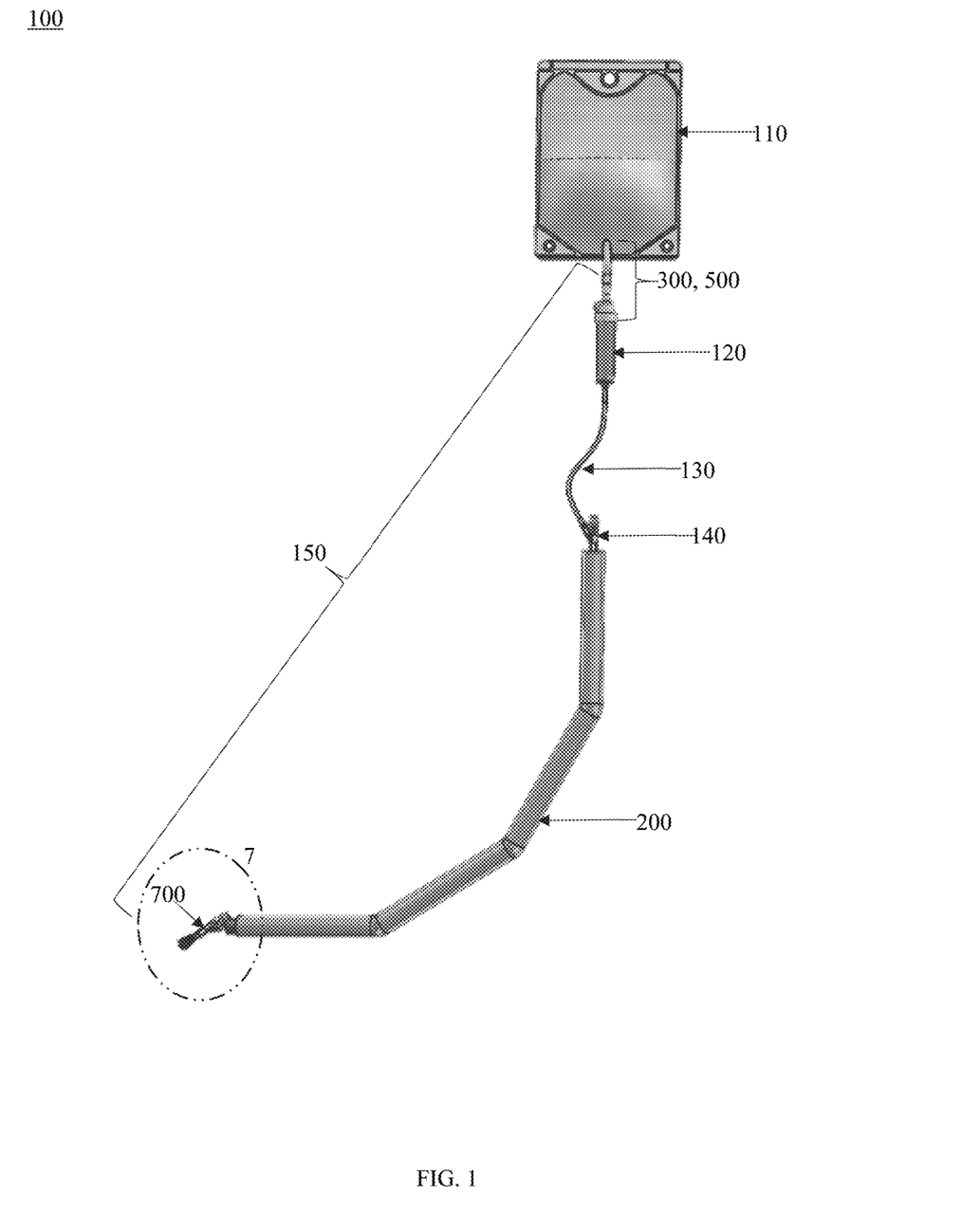
FIG. 1 shows an example of a system according to embodiments connected to a medical fluid container.

FIG. 1 shows an example 100 of medical fluid delivery system 150, according to embodiments, connected to a medical fluid container 110 via its port. The medical fluid container 110 may be any medical fluid (e.g., intravenous or infusion fluid) container, bag, etc. As shown in FIG. 1, the system 150 may include a fluid connection device 200 connected to a fluid access device 300, 500. In some embodiments, the fluid access device 300, 500 may be configured to puncture the medical fluid container 110 through its complimentary port.

In some embodiments, a drip chamber 120 and a conduit (e.g., tubing) 130 may be connected to the fluid access device 300, 500 and a port 140 disposed on an end of the fluid connection device 200. In some embodiments, the drip chamber 120 may be any available drip chamber capable of visually determining the drop flow rate of the medical (IV) fluid. For example, the drip chamber may include but is not limited to a microdrip (e.g., 60 gtts/mL) chamber, a macrodrip (e.g., 8 to 20 gtts/ML) chamber, as well as other available drip chambers. The conduit 130 may be configured to be control the rate of flow, for example, by including a clamp. The conduit 130 may be any tubing compatible with the drip chamber and port. For example, in some embodiments, the conduit 130 may be about 1-3 inches. As used herein, "conduit," "tube", and "line", refer generally to any conduit that could be used in a medical setting or a patient care environment including, but not limited to, IV tubes, fluid-carrying tubes and the like.

In some embodiments, a port 700 may be connected on the other end of the fluid connection device 200. The port 700 may be capable of connecting to the patient, for example, by a vascular access device.

Figure 2A:
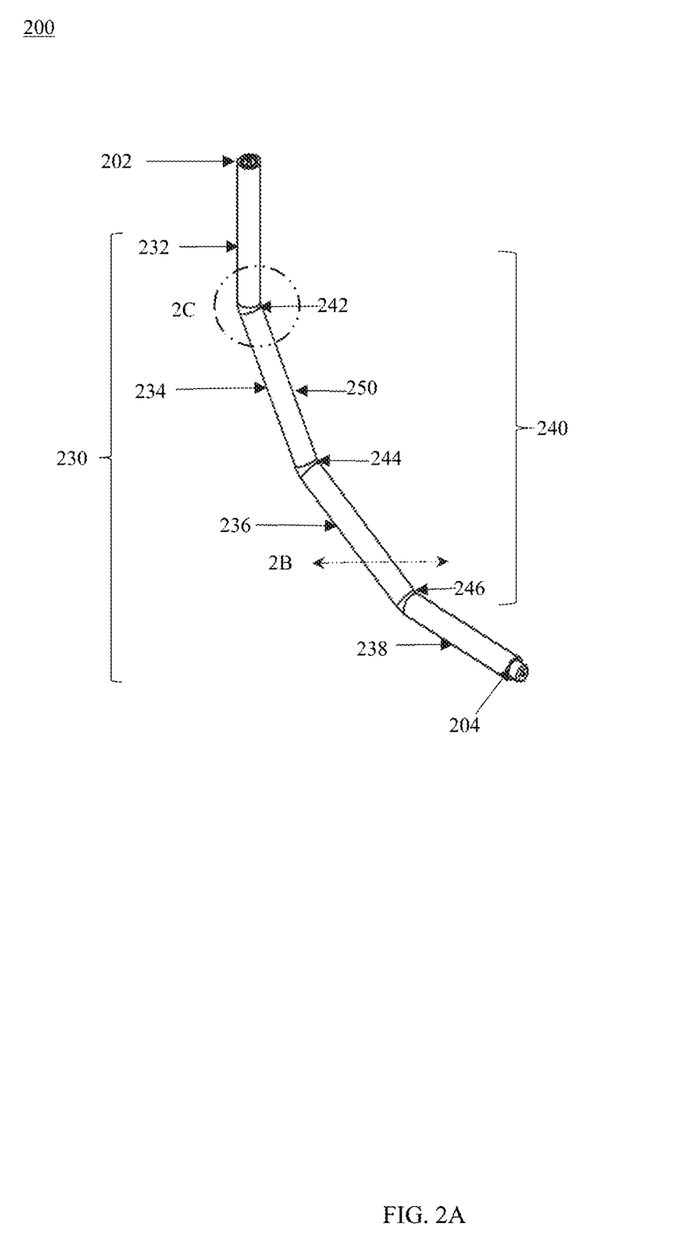
Figure 2B:
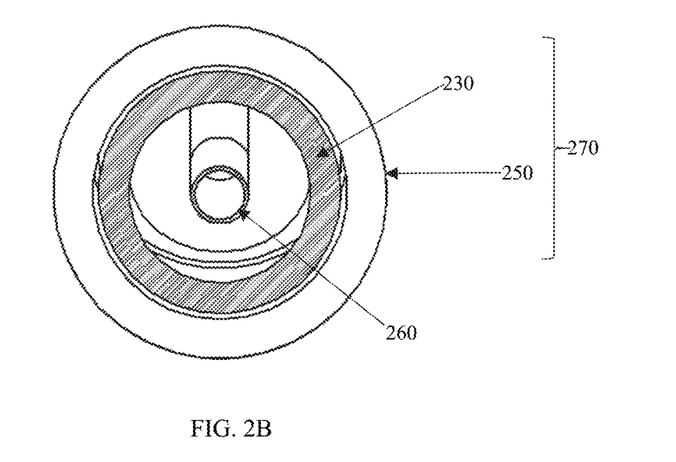
Figure 2C:
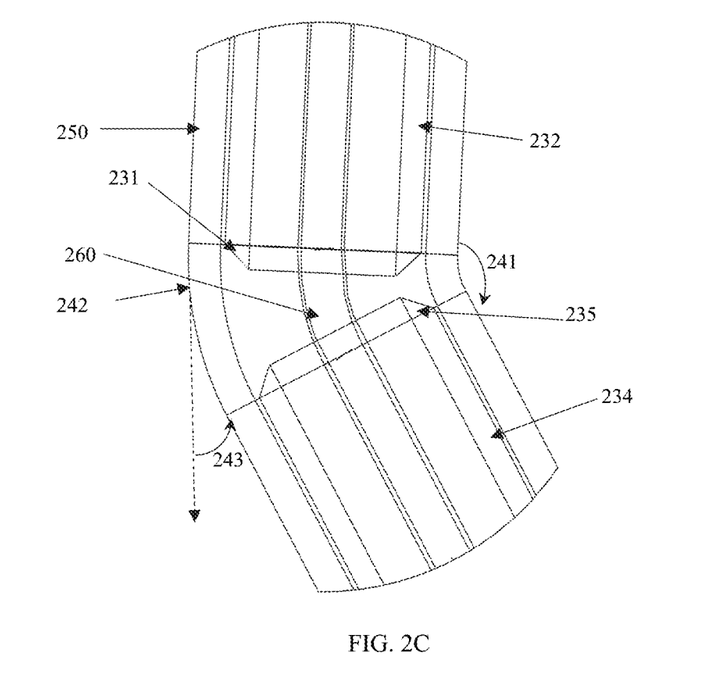
FIG. 2C shows a cross-sectional view of the fluid connection device shown in FIG. 2A.

FIGS. 2A-C show additional views of the fluid connection device 200 according to embodiments. In some embodiments, the fluid connection device 200 may include a first end 202, a second end 204, and a length therebetween. In some embodiments, an port or adapter may be disposed on each end to connect to the respective components. For example, as shown in FIG. 1, the port 140 may be disposed on the first end 202 to connect to the medical fluid container 110 and the port 700 may be connected to the second end 204 to connect to a vascular access device provided on the patient.

In some embodiments, the fluid connection device 200 may include a fluid conduit 260 disposed along the length and a housing 270 disposed along the length and surrounding the fluid conduit 260. In some embodiments, the housing 270 may include a plurality of rigid segments 230 spaced apart and at least one joint segment 240 may be disposed at least between each pair of rigid segments within that space.

In some embodiments, the housing 270 may include any number of rigid and joint segments. For example, as shown in FIG. 2A, the plurality of rigid segments 230 may include four rigid segments: a first rigid segment 232, a second rigid segment 234, a third rigid segment 236 and a fourth rigid segment 238. The plurality of joint segments 240 may include three joint segments: a first joint segment 242 disposed between the first rigid segment 232 and the second rigid segment 234; a second joint segment 244 disposed between the second rigid segment 234 and the third rigid segment 236; a third joint segment 246 disposed between the third rigid segment 236 and the fourth rigid segment 238. The housing may include less and/or more rigid segments and/or joint segments.

In some embodiments, the rigid segments 230 may be elongated segments having a central lumen in which the fluid conduit 260 may be disposed. In some embodiments, the rigid segments 230 may each have the same length and same radius. For example, the length of each rigid segment 230 may be 5 inches or less. In some embodiments, one or more of the rigid segments may have different lengths.

In some embodiments, the joint segments 240 may include a central lumen in which the fluid conduit 260 may be disposed as shown in FIGS. 2A-2C.

In some embodiments, the joint segments 240 may be an elongated segment that is configured to bend to a predetermined bending angle, as shown in FIGS. 1-2C. The joint segments 240 may be configured to move between an elongated configuration and a bent configuration with respect to one of the rigid joints 230. FIGS. 1-2C show all joint segments 240 in the bent configuration. In some embodiments, each joint segment 240 may have a predetermined bending angle. The predetermined bending angle may be about 30 degrees to about 70 degrees. In some embodiments, the predetermined bending angle may be about 70 degrees or less.

In some embodiments, the joint segments 240 may be incapable of bending radially (e.g., twisting). This way, the joint segments 240 may be configured to only linearly bend with respect to the at least one of the rigid segments 230 (e.g., the preceding rigid segment) to the predetermined bending angle.

For example, as shown in FIG. 2C, the joint segment 242 may be configured to bend to the predetermined (or predefined) bending angle 243 with respect to the first rigid segment 232. In the example shown in FIG. 2C, the predetermined bending angle 243 may be about 30 degrees so that a corresponding bending angle 241 is about 150 degrees. In some embodiments, the bending angle 243 may be about 70 degrees or less and the corresponding bending angle 241 may be about 110 degrees or more. In some embodiments, the joint segments 240 may have the same predetermined bending angle 243. In some embodiments, the predetermined bending angle 243 of each joint segment 240 may be defined by the length of the rigid segments. In some embodiments, one or more of the joint segments 240 may have different predetermined angles, among others, or a combination thereof.

In some embodiments, one or more of the joint segments 240 may be a curved segment so that each joint segment may be bent in its default configuration.

In some embodiments, the housing 270 may include an outer casing 250 that covers the fluid conduit 260 and the rigid segments 230, for example, as shown in FIGS. 2A-2C. In some embodiments, the outer casing 250 may extend the length of the device from end 202 to end 204. In some embodiments, the outer casing 250 may include the joint segments 240, as shown in FIG. 2C. In this example, the diameter of the joint segments 240 may be the same as the outer casing 250.

In further examples, the rigid segments 230 may further include angled sides at the respective ends. The angled sides of the ends may be configured to prevent kinking of the fluid conduit 260 when the joint segments 240 are bent.

For example, FIG. 2C shows an example of an enlarged cross-sectional view of a pair of rigid segments (e.g., 232 and 234) separated by a joint segment (e.g., 242). As shown in this figure, the first rigid segment 232 and the second rigid segment 234 may have angled sides 231 and 235 at their respective ends. Also, as shown in this figure, the first joint segment 242 may be a part of the casing 250 and the joint segment 242 may be disposed between the first rigid segment 232 and the second rigid segment 234. Like the other joint segments, the first joint segment 242 may have the predetermined bending angle 243 (e.g., about 30 degrees).

In some embodiments, the outer casing 250 may be omitted. For example, the joint segments 240 may be in the same layer as the rigid segments 230 so that the rigid segments 230 and the joint segments 240 have substantially the same outer diameter. By way of example, the joint segments 240 and the rigid segments 230 may be manufactured so as to be integrated.

In some embodiments, the fluid connection device 200 may be made of one or more materials including but not limited to polyvinyl chloride (PVC), polyethylene, polypropylene plastic, vinyl, other synthetic polymers, among others, or a combination thereof. For example, the fluid conduit 260 may be made of PVC, polyethylene, polypropylene plastic, among others, or a combination thereof. The fluid conduit 260 may also have diameters according to current medical standards. By way of another example, the rigid segments 230 may be made of PVC, among others, or a combination thereof. The outer casing 250 and/or the joint segments 240 may be made of vinyl, among others, or a combination thereof. In some embodiments, the outer casing 250 and/or the joint segments 240 may be made of one or more materials so that the outer casing 250 and/or the joint segments 240 may be less rigid (or more flexible) than the rigid segments 230.

In some embodiments, the outer casing 250 and/or the joint segments 240 may be fixedly disposed to the rigid segments 230 (e.g., epoxy), co-extruded, among others, or any combination thereof. In some embodiments, the housing 270 may be fixedly disposed to the fluid conduit 260, for example, by a fastener (e.g., epoxy, adhesive, etc.), by a fixedly disposed adapter/ports (e.g., ports 140 and 700) disposed at the respective ends of the housing 270 and conduit 260, among others, or a combination thereof.

The fluid connection device 200 according to embodiments can be ligature resistant, tamper-proof and weaponization resistant. For example, the dimensions of the rigid segments 230 and/or the joint segments 240 can provide for ligature resistance so as to prevent possible strangulation, hanging, among others, or a combination thereof. The length of the rigid segments 230 with respect to each joint segment 240 can ensure the angle of the joint segments 240 cannot be manipulated beyond a predetermined bending angle (e.g., beyond 70 degrees). Additionally, by restricting the bending angle of the joint segments 240 (e.g., to about 70 degrees), the fluid connection device 200 cannot be tied or swung over a ligature point, thereby preventing the use of the fluid connection device 200 for hanging.

For example, the fluid connection device 200 can provide for tamper-proof resistance by preventing disassembly, preventing swallowing, and preventing kinking that may obstruct medical fluid flow. The manufacturing of the fluid connection device 200 can be configured to prevent disassembly. The dimensions of the components (e.g., rigid segments, joint segments 240, etc.) of the fluid connection assembly cannot easily occlude the trachea in the unlikely event that the device 200 is disassembled in any way. By restricting the bending angle of the joint segments 240 (e.g., to about 70 degrees), the fluid connection device 200 can prevent kinking of the fluid conduit 260 that could lead to occlusion of flow of the medication fluid (e.g., from the container 100).

By way of another example, the dimensions of the rigid segments 230 and/or the joint segments 240 can provide for weaponization resistance so as to prevent the use of the device 200 as being used as a whip. For example, the rigidity of the rigid segments 230, the length of the rigid segments 230, the predetermined bending angle (e.g., about 30 to 70 degrees) of each joint segment 240, among others, or any combination thereof, can slow the speed of articulation of each rigid joint 230 at each joint segment 240 so as to reduce whip-like characteristics.

Figure 3A:
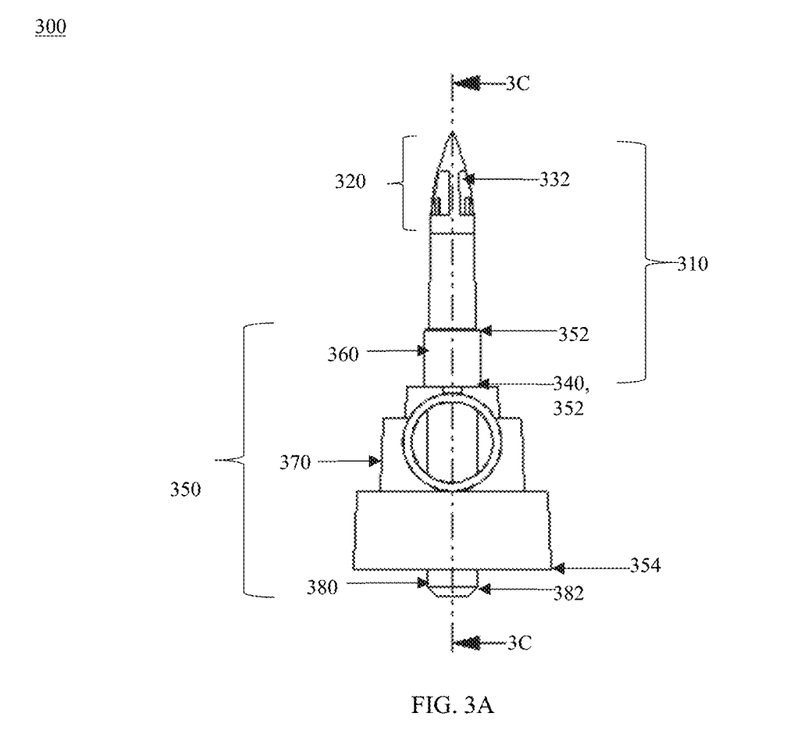
Figure 5A:
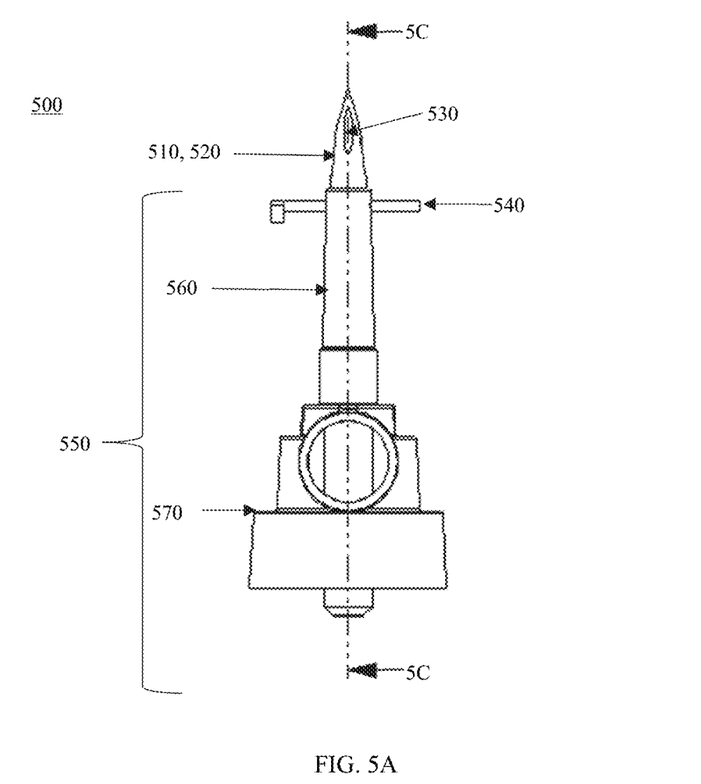

In some embodiments, the system 110 may also include an access member (300, 500) that is configured to provide for weaponization resistance. In some embodiments, the access member (300, 500) may include a spike member having a puncturing point and a base member having an sleeve. The spike member may be configured to be breakaway (i.e., detachable) and/or retractable with respect to the shaft of the base member. By inhibiting access to the spike member, the risk of using the puncturing point as a sharp weapon can be mitigated.

Figure 3B:
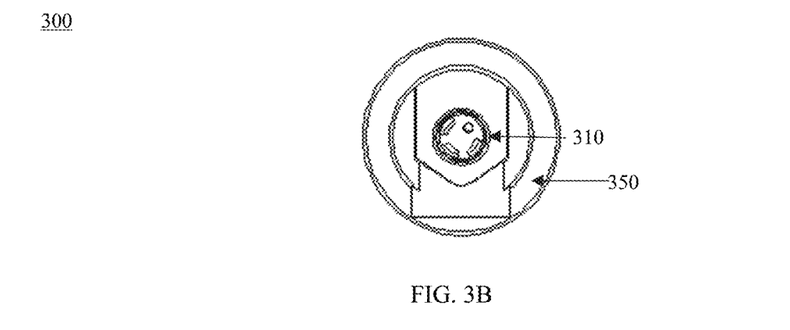
Figure 3C:
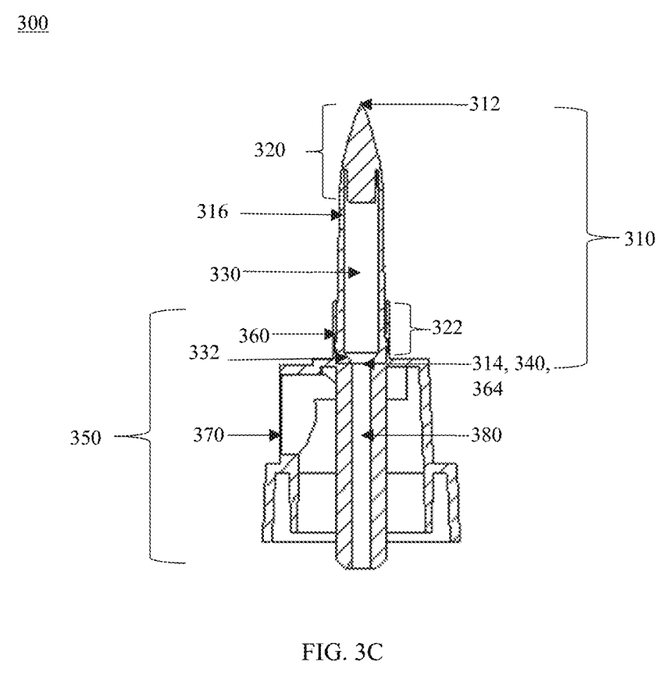
FIG. 3C shows a cross-sectional view of the access device shown in FIG. 3A.
Figure 4A:
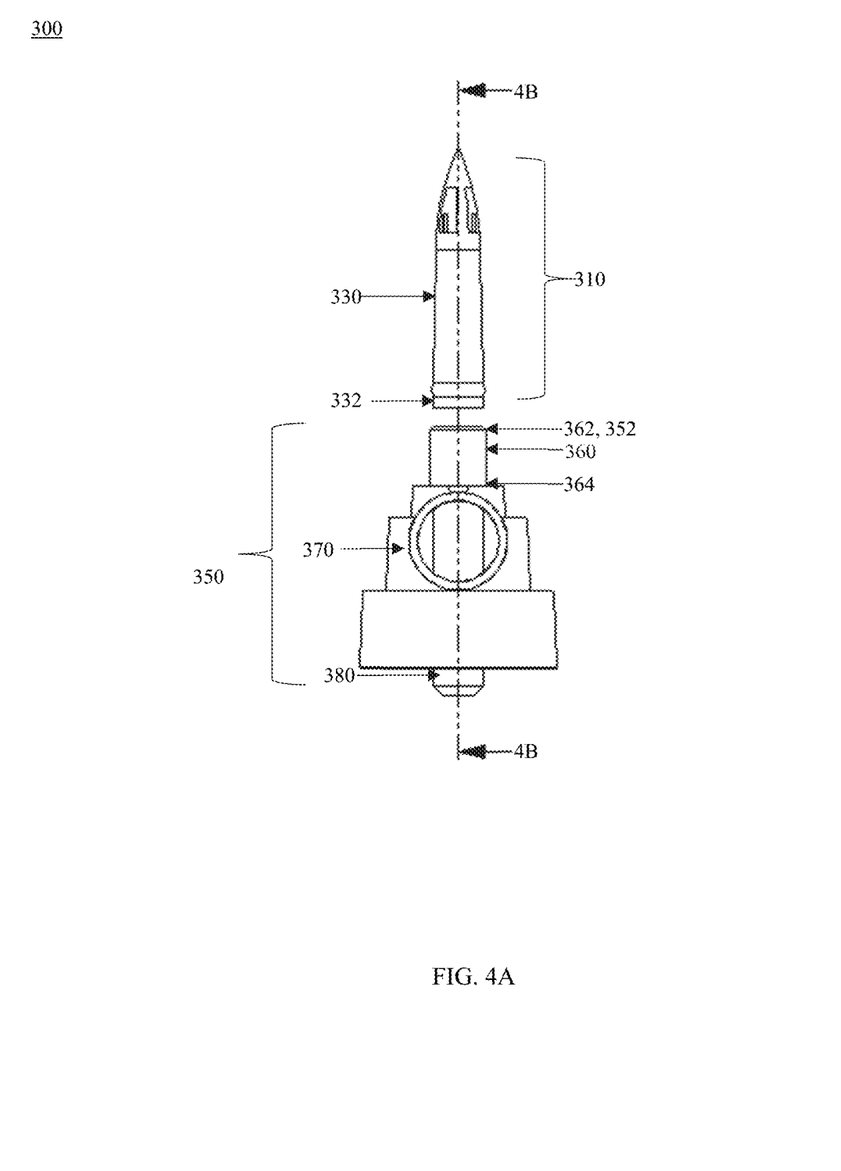
FIGS. 4A and B show views of the access device shown in FIGS. 3A-C in a breakaway state according to embodiments.
Figure 4B:
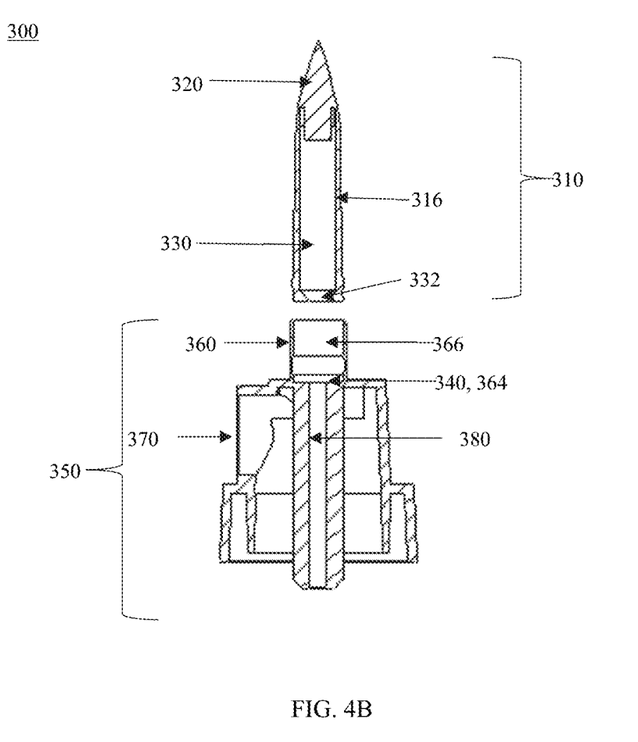
FIG. 4B shows a cross-sectional view of the access device shown in FIG. 4A.

FIGS. 3A-4B show an example of the access member 300 that includes a breakaway spike member 310 according to embodiments. FIGS. 3A-C show views of the access member 300 in its default (also referred to as "first") state (e.g., the spike member 310 attached to a base member 350). In this state, the spike member 310 may be used to puncture a complimentary port/adapter of a medical fluid container (e.g., container 110). FIGS. 4A and 4B show views of the access member 300 in its detached (also referred to as "second") state with the spike member 310 detached from the base member 350. After the spike member 310 is inserted into the complimentary port/adapter of the medical fluid container and a user (e.g., patient) tries to remove the spike member 310 from the fluid container via the attached fluid connection device (e.g., the fluid connection device 200 or other IV/medical fluid conduit/tubing), the spike member 310 may be configured detach from the base member 350 and remain in the fluid container (e.g., fluid container 110) upon exertion of that force. This way, the access member 300 can allow a clinician to pierce a medical fluid container with ease but remove any potential access, for example, by a patient, to the spike member 310.

In some embodiments, the access member 300 may include the spike member 310 that is configured to be detached/breakaway from the base member 350. As shown in FIGS. 3A-4B, the spike member 310 may include a first end 312, a second end 314, and a length 316 therebetween. The spike member 310 may include a puncturing tip 320 disposed at the first end 312. In some embodiments, the spike member 310 may include a fluid channel 330 disposed along the length 316 of the access member 300. In some embodiments, the spike member 310 may include an inlet 332 on the puncturing tip 320 that opens to the fluid channel 330 and a tapered outlet 332 of the channel 330 at the second end 314. The diameter of the tapered outlet 332 may be smaller than the diameter of the channel 330. The spike member 310 may include a portion 322 that is disposed within the base member. In some embodiments, the portion 322 may include a portion of the channel 330 and the tapered outlet 332.

In some embodiments, the base member 350 may have a first end 352, a second end 354, and a length therebetween. The base member 350 may include a shaft 360 configured to receive a portion of the spike member 310 and a body 370 from which the shaft 360 extends therefrom. The shaft 360 may be disposed at the first end 352. In some embodiments, the shaft 360 may include a first end 362, a second end 364, and a length therebetween. In some embodiments, the shaft 360 may include a channel 366 in which the portion 322 of the spike member 310 is disposed. The portion 322 may be disposed entirely along the length of the shaft 360 so that the second end 314 of the spike member 310 is disposed at the second end 362 of the shaft 360.

In some embodiments the base member 350 may include a fluid channel 380 disposed along the length of the body 370 that is configured to communicate/connect to the fluid channel 330 of the spike member 310 when the spike member 310 is attached. In some embodiments, the diameter of the channel 380 may correspond to the smallest diameter of the tapered outlet 332.

In some embodiments, the channel 380 may extend past the body 370. In some embodiments, the channel 380 may have an adapter 382 configured to connect to a drip chamber (e.g., drip chamber 120).

In some embodiments, the spike member 310 can be configured to separate from the base member 350 (breakaway) at a connection point 340 upon a pulling force. The connection point 340 may correspond to point where the spike member 310 is attached to the second end 364 of the shaft 360, for example, using one or more materials having frangible properties so that the spike member 310 can separate from the shaft 360 at the connection point 340 upon a pulling force. For example, the one or more materials may include but is not limited to silicone, an adhesive, plastic, rubber, among others, or a combination thereof. This way, the connection point 340 may be made of one or more materials that are weaker than the spike member 310 and the base member 350.

FIGS. 4A and 4B show the spike member 310 in the detached or breakaway (also referred to as "second") state where the spike member 310 is detached/separated from the base member 350. By way of example, in use, when the access device 300 is disposed in a medical fluid container so that the spike member 310 is disposed in the port of the medical fluid container, the spike member 310 may breakaway from the base member 350 at the connection joint 340 when the attached medical fluid connection device (e.g., 200) is pulled resulting in the spike member 310 be fixed in the port of the medical fluid. This way, only the base member 350 can be accessible.

FIGS. 5A-6B show an example of the access member 500 that includes a retractable spike member 510 according to embodiments. FIGS. 5A-C show views of the access member 500 in it is default (also referred to as "first") state (e.g., the spike member 510 is extending from a base member 550 with a pin 540 attached/coupled to a spring 542). In this state, the spike member 510 may be used to puncture a complimentary port/adapter of a medical fluid container (e.g., container 110). In this state, the pin 540 may hold the spring 542 disposed in the spike member 510 in place in an elongated position by latching its hook 544. After the spike member 510 is inserted into a port of a medical fluid container (e.g., 110) to the pin 540 (so that the pin 540 is against the bottom of that port), the pin 540 may be removed so as to permanently activate retraction of the spike member 510 into the base member 550 by causing the spring 542 to retract to its neutral position, resulting in the spike member 510 being in the retracted (also referred to as "second") state.

Figure 6A:
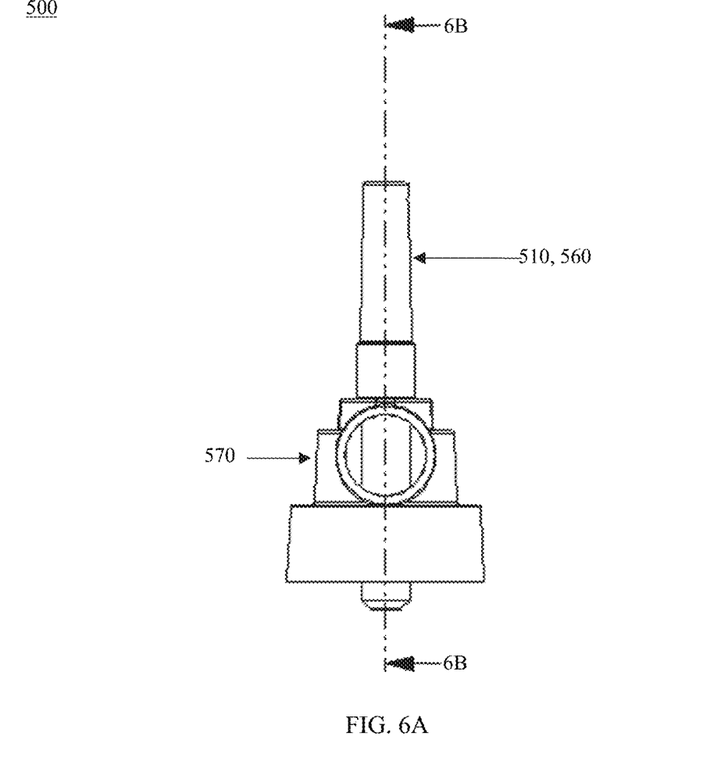
FIGS. 6A and B show views of the access device shown in FIGS. 5A-C in a retractable state according to embodiments.
Figure 6B:
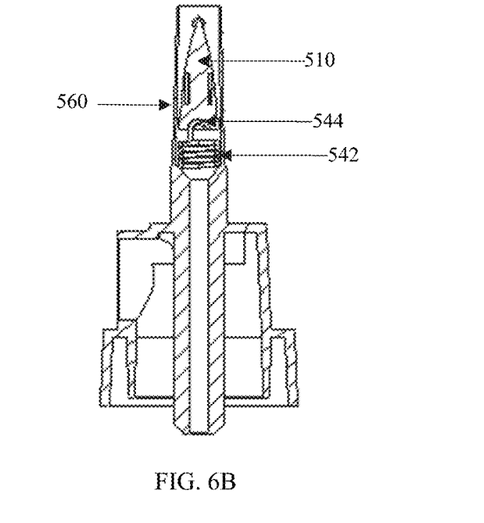
FIG. 6B shows a cross-sectional view of the access device shown in FIG. 6A.

FIGS. 6A and 6B show views of the access member 500 in the retracted state where the spike member 510 is retracted into the base member 550. After the spike member 510 is inserted into the complimentary port/adapter of the medical fluid container (e.g., 110) and caused to be moved to its retracted state (i.e., the pin 540 removed) and a user (e.g., patient) tries to remove the access member 500 from the fluid container (e.g., 110) via the attached fluid connection device (e.g., the fluid connection device 200 or other IV/medical fluid conduit/tubing), the spike member 510 would not be accessible if successfully pulled from the fluid container. This way, the access member 500 can allow a clinician to pierce a medical fluid container with ease but remove any potential access, for example, by a patient, to the spike member 510.

In some embodiments, the access member 500 may include the spike member 510 that is configured to be retractable with respect to the base member 550. As shown in FIGS. 5A-6B, the spike member 510 may include a first end 512, a second end 514, and a length 516 therebetween. The spike member 510 may include a puncturing tip 520 disposed at the first end 512. In some embodiments, the spike member 510 may include an opening 534 disposed at the second end 514 in which the pin 540 can be disposed. In some embodiments, the spike member 510 may include an inlet 532 on the puncturing tip 520 that communicates with a fluid channel 566 of a shaft 560 of the base member 550.

Figure 5B:
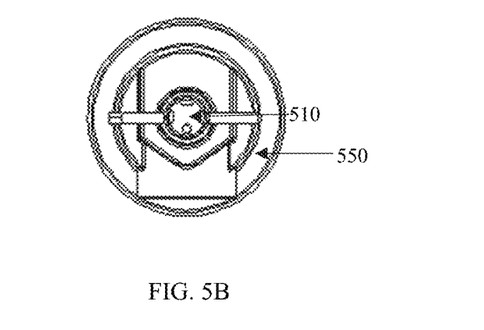
Figure 5C:
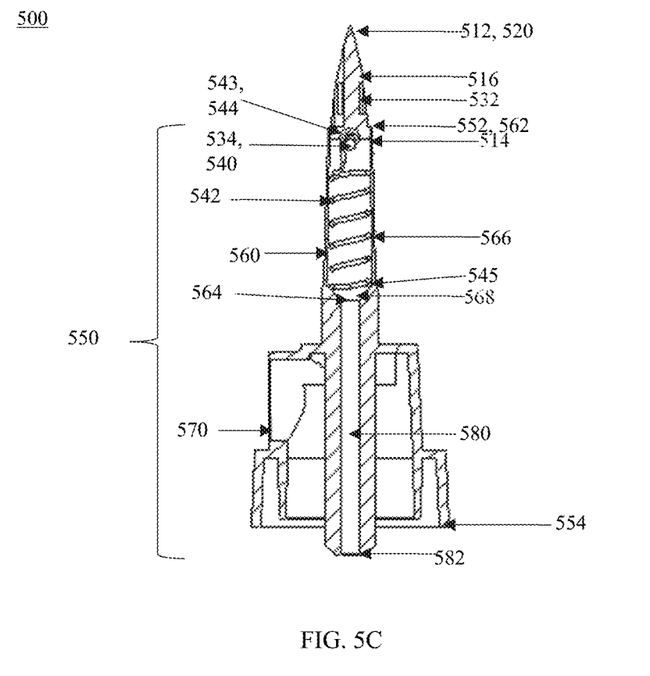
FIG. 5C shows a cross-sectional view of the access device shown in FIG. 5A.

In some embodiments, the base member 550 may have a first end 552, a second end 554, and a length therebetween. The base member 550 may include a shaft 560 configured to receive the spike member 510 and a body 570 from which the shaft 560 extends therefrom. The shaft 560 may be disposed at the first end 552. In some embodiments, the shaft 560 may include a first end 562, a second end 564, and a length therebetween. In some embodiments, the shaft 560 may include the channel 566 in which the spike member 510 is disposed when the pin 540 is removed. In some embodiments, the channel 566 may include a tapered portion/outlet 568 that is disposed at the end 564.

In some embodiments the base member 550 may include a fluid channel 580 disposed along the length of the body 570 that is configured to communicate/connect to the fluid channel 566. In some embodiments, the channel 580 may be fluidly connected to the channel 566. In some embodiments, the diameter of the channel 580 may correspond to the smallest diameter of the tapered portion/outlet 568.

In some embodiments, the channel 580 may extend past the body 570. In some embodiments, the channel 580 may have an adapter 582 configured to connect to a drip chamber (e.g., drip chamber 120).

In some embodiments, the access member 500 may include a spring 542 disposed on the spike member 510 and within the channel 566 of the shaft 560. The spring 542 may include a first end 543 and a second end 545. In some embodiments, the spring 542 may include a hook 544 disposed at the first end 543. The hook 544 may be fixedly attached to the spike member 510 to surround the opening 534. The hook 544 may be configured to be disposed/latched on the pin 540. In some embodiments, the second end 545 may be connected to the second end 564 of the shaft 560. This way, the spike member 510 may be attached to the base member 550 via the spring 542.

In the default (first) state, the pin 540 may be disposed in the opening 534 so that the hook 544 is latched onto the pin 540. In this state, the spring 542 may be an elongated position so that the spike member 510 protrudes from the shaft 560. In the default or first state, the spring 542 may be in a default or elongated state. In this position, the spike member 510 may be configured to puncture a medical fluid container.

As shown in FIGS. 6A and 6B, after the pin 540 is removed, in the second state, the spring 542 retracts toward the second end 564 causing the spike member 510 to retract into the shaft 560. In the second state, the spring 542 may be in a recoiled state. In some embodiments, in the second state, the entire length of the spike member 510 may be disposed within the shaft 560 so that the puncturing tip 520 is not accessible.

In some embodiments, the pin 540 may be made of a semi-rigid material.

Figure 7:
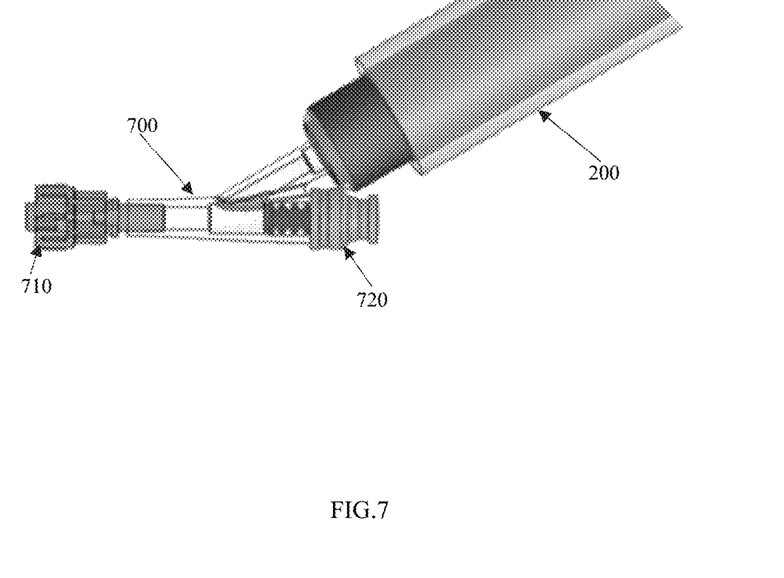
FIG. 7 shows an example of an adapter/port shown in FIG. 1 according to embodiments.

In some embodiments, the system 110 may include the port 700 disposed at the end 204 of the fluid connection device 200. FIG. 7 shows an example of the port 700 according to embodiments. In some embodiments, the port 700 may be an access port 710 disposed on one end and an sterile-capped adapter 720 on the other end. In some embodiments, the system 110 may include a different port.

The systems may also be adapted for use with other medical fluid containers, medical fluid delivery devices, ports, adapters, access devices, among others, or a combination thereof. For example, the fluid connection device according to embodiments may be used with additional and/or alternative medical fluid containers, medical fluid delivery devices (e.g., infusion pumps, inflatable pressure infusers with a medical bag, etc.), in-line filters, among others, or a combination thereof.

In some embodiments, the fluid connection device 200 may be provided with adapters on each end so as to capable of being connected to other medical fluid containers, access devices, adapters, ports, among others, or a combination thereof. In some embodiments, the access devices 300, 500 may be provided with an adapter (with and/or without the drip chamber and conduit) so as to be capable of being connected to other fluid connection devices.

In some embodiments, the devices of the system and/or the system may individually or collectively be sterilized according to medical standards.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed is:

1. An intravenous administration system, comprising:
    a fluid connection device having a first end, a second end, and a length, the fluid connection device including:
        an internal conduit configured to deliver a medical fluid and disposed along the length; and
        a housing disposed along the length and having a channel in which the internal conduit is disposed, wherein the housing includes:
            more than one rigid segments, each rigid segment being an elongated segment, the more than one rigid segments including a first rigid segment and a second rigid segment spaced from the first rigid segment;
            one or more joint segments, each joint segment being an elongated segment configured to bend to a predetermined bending angle with respect to at least one rigid segment, the one or more joint segments including a first joint segment disposed between the first rigid segment and the second rigid segment and configured to bend to the predetermined bending angle with respect to the first rigid segment; and
            a casing that surrounds the more than one rigid segments;
            wherein the casing includes the one or more joint segments; and
            wherein the casing is less rigid than the more than one rigid segments.

2. The intravenous administration system according to claim 1, wherein the predetermined bending angle is at least about thirty degrees.

3. The intravenous administration system according to claim 2, wherein the predetermined bending angle is about seventy degrees or less.

4. The intravenous administration system according to claim 3, further comprising:
    an access device connected to one end of the fluid connection device;
    wherein the access device includes:
        a spike member, the spike member including a puncturing tip; and
        a base member, the base member including a body and a shaft extending from the body;
    wherein the spike member is disposed within the shaft in a first state and is configured to move from the first state to a second state with respect to the shaft.

5. The intravenous administration system according to claim 4, wherein:
    the spike member includes a portion disposed within the shaft of the base member in the first state;
    the spike member is configured to move from the first state to the second state with respect to the shaft upon exertion of force;
    in the first state, the spike member is attached to the shaft; and
    in the second state, the spike member is detached from the shaft at a connection point.

6. The intravenous administration system according to claim 5, wherein the spike member is configured to remain in a medical fluid container when connected and the force is exerted to remove the access device from the medical fluid container causing the spike member to move from the first state to the second state.

7. The intravenous administration system according to claim 4, wherein:
    upon removal of a pin, the spike member is configured to move from the first state to the second state with respect to the shaft;
    in the first state, the spike member extends from the shaft; and
    in the second state, the spike member is permanently retracted within the shaft.

8. The intravenous administration system according to claim 1, wherein:
    each rigid segment includes a first end and a second end; and
    the first end and the second end of the rigid segment has angled sides.

9. An intravenous administration system, comprising:
    an access device configured to connect to one end of a fluid connection device;
    wherein the access device includes:
        a spike member, the spike member including a puncturing tip; and
        a base member, the base member including a body and a shaft extending from the body;
    wherein the spike member is disposed within the shaft in a first state and is configured to move from the first state to a second state with respect to the shaft;
    wherein the spike member is configured to move from the first state to the second state with respect to the shaft upon removal of a pin;
    wherein in the first state, the spike member extends from the shaft; and
    wherein in the second state, the spike member is retracted within the shaft.

10. The intravenous administration system according to claim 9, further comprising:
    a drip chamber attached to the access device; and
    a drip conduit connected to the drip chamber.

11. The intravenous administration system according to claim 9, wherein:
    in the second state, the spike member is permanently retracted within the shaft.

12. The intravenous administration system according to claim 11, wherein the access device further includes:
    a spring including a first end attached to the spike member and a second end attached to the shaft, the spring including a hook disposed at one end; and
    the pin inserted through the spike member to engage the hook in the first state;
    wherein the spring is configured to permanently move from a default state when the pin engages the hook in the first state so that the spring is elongated to a recoiled state when the pin is removed from the spike member;
    wherein the spike member protrudes from the shaft in the default state and the first state; and
    wherein the spike member retracts entirely within the shaft when the spring is in the recoiled state and the second state.

13. The intravenous administration system according to claim 12, wherein;
the access member is configured to be in the second state after being attached to a medical fluid container.

14. An intravenous administration system, comprising:
a fluid connection device having a first end, a second end, and a length, the fluid connection device including:
an internal conduit configured to deliver a medical fluid and disposed along the length; and
a housing disposed along the length and having a channel in which the internal conduit is disposed, wherein the housing includes:
more than one rigid segments, each rigid segment being an elongated segment, the more than one rigid segments including a first rigid segment and a second rigid segment spaced from the first rigid segment;
one or more joint segments, each joint segment being an elongated segment configured to bend to a predetermined bending angle with respect to at least one rigid segment, the one or more joint segments including a first joint segment disposed between the first rigid segment and the second rigid segment and configured to bend to the predetermined bending angle with respect to the first rigid segment; and
a casing that surrounds the more than one rigid segments;
wherein the casing includes the one or more joint segments; and
wherein the casing is less rigid than the more than one rigid segments; and
an access device configured to connect to one end of the fluid connection device, wherein the access device includes:
a spike member, the spike member including a puncturing tip; and
a base member, the base member including a body and a shaft extending from the body;
wherein the spike member is disposed within the shaft in a first state and is configured to move from the first state to a second state with respect to the shaft.

15. The intravenous administration system according to claim 14, wherein:
the predetermined bending angle is about thirty degrees.

16. The intravenous administration system according to claim 15, wherein the predetermined bending angle is about seventy degrees or less.

17. The intravenous administration system according to claim 14, wherein:
the spike member includes a portion disposed within the shaft of the base member in the first state; and
the spike member is configured to move from the first state to the second state with respect to the shaft upon exertion of force;
in the first state, the spike member is attached to the shaft; and
in the second state, the spike member is detached from the shaft at a connection point.

18. The intravenous administration system according to claim 17, wherein the spike member is configured to remain in a medical fluid container when connected and the force is exerted to remove the access device from the medical fluid container causing the spike member to move from the first state to the second state.

19. The intravenous administration system according to claim 14, wherein:
the spike member is configured to move from the first state to the second state with respect to the shaft upon removal of a pin;
in the first state, the spike member extends from the shaft; and
in the second state, the spike member is permanently retracted within the shaft.

* * * * *